United States Patent
Merriman et al.

(10) Patent No.: US 10,597,767 B2
(45) Date of Patent: Mar. 24, 2020

(54) NANOPARTICLE FABRICATION

(71) Applicant: Roswell Biotechnologies, Inc., San Diego, CA (US)

(72) Inventors: Barry L. Merriman, San Diego, CA (US); Paul W. Mola, San Diego, CA (US); Chulmin Choi, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

(21) Appl. No.: 15/050,270

(22) Filed: Feb. 22, 2016

(65) Prior Publication Data

US 2017/0240962 A1   Aug. 24, 2017

(51) Int. Cl.
| | |
|---|---|
| *C23C 14/04* | (2006.01) |
| *C23C 14/58* | (2006.01) |
| *B22F 1/00* | (2006.01) |
| *C12Q 1/6874* | (2018.01) |
| *C23C 14/16* | (2006.01) |

(52) U.S. Cl.
CPC .......... *C23C 14/042* (2013.01); *B22F 1/0018* (2013.01); *C12Q 1/6874* (2013.01); *C23C 14/165* (2013.01); *C23C 14/5806* (2013.01); *B22F 2998/10* (2013.01)

(58) Field of Classification Search
CPC ... C12Q 1/6874; C23C 16/06; C23C 14/5806; C23C 16/56; C23C 14/16
USPC .............. 427/123, 404, 97.4, 99.2, 125, 256
See application file for complete search history.

(56) References Cited

U.S. PATENT DOCUMENTS

| | | | | |
|---|---|---|---|---|
| 5,082,627 A | | 1/1992 | Stanbro | |
| 5,194,133 A | | 3/1993 | Clark et al. | |
| 5,366,140 A | * | 11/1994 | Koskenmaki | ........... H01L 24/29 228/246 |

(Continued)

FOREIGN PATENT DOCUMENTS

| | | |
|---|---|---|
| CN | 104685066 | 6/2015 |
| CN | 104703700 | 6/2015 |

(Continued)

OTHER PUBLICATIONS

Fink et al. "Electrical conduction through DNA molecules". Nature. vol. 398 (1999). pp. 407-410.*

(Continued)

*Primary Examiner* — Jose Hernandez-Kenney
(74) *Attorney, Agent, or Firm* — Snell & Wilmer L.L.P.

(57) ABSTRACT

Methods for fabricating at least one nanoparticle include providing one or more substrates and depositing a substance on the one or more substrates. At least one portion of the substance is heated or annealed so the at least one portion beads up on the one or more substrates due to cohesive forces of the substance being greater than adhesive forces between the substrate and the substance. In some methods, a pattern generation process is performed to define the at least one portion. A combination of a substance material for the substance and a substrate material for the one or more substrates may also be selected so that the at least one portion beads up into a predetermined shape. The substance may also be deposited on the one or more substrates with a sub-monolayer thickness or with gaps to further reduce a nanoparticle size.

7 Claims, 16 Drawing Sheets

(56) References Cited

U.S. PATENT DOCUMENTS

| | | |
|---|---|---|
| 5,414,588 A | 5/1995 | Barbee, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,767,687 A | 6/1998 | Geist |
| 5,871,918 A | 2/1999 | Thorp et al. |
| 5,881,184 A | 3/1999 | Guidash |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,108,880 B2 | 8/2015 | Jin et al. |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0064390 A1 | 4/2003 | Schülein et al. |
| 2003/0087296 A1 | 5/2003 | Fujita et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0151541 A1 | 7/2005 | Brinz et al. |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0098815 A1 | 5/2008 | Merassi et al. |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0062684 A1 | 3/2009 | Gregersen et al. |
| 2009/0152109 A1 | 6/2009 | Whitehead et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1* | 6/2010 | Tomaru .............. G01N 21/658 356/301 |
| 2010/0184062 A1 | 7/2010 | Steinmuller-Nethl et al. |
| 2010/0188109 A1 | 7/2010 | Edel et al. |
| 2010/0194409 A1 | 8/2010 | Gao et al. |
| 2010/0206367 A1 | 8/2010 | Jeong et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci et al. |
| 2011/0076783 A1 | 3/2011 | Liu et al. |

(56) References Cited

U.S. PATENT DOCUMENTS

| | | |
|---|---|---|
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1* | 9/2011 | Jin ................... B81C 1/00206 428/34.1 |
| 2011/0233075 A1 | 9/2011 | Soleymani et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2013/0049158 A1 | 2/2013 | Hong et al. |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1* | 10/2013 | Neretina ............... B05D 1/32 428/212 |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1* | 1/2014 | Jin .................... B05D 5/08 428/297.4 |
| 2014/0018262 A1 | 1/2014 | Reda et al. |
| 2014/0027775 A1 | 1/2014 | Quick et al. |
| 2014/0048776 A1 | 2/2014 | Huang et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0367749 A1 | 12/2014 | Bai et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0068892 A1 | 3/2015 | Ueno et al. |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1* | 9/2015 | Lewis ............... H01L 31/03521 257/21 |
| 2015/0293025 A1* | 10/2015 | Ninomiya ............. C23C 14/562 356/244 |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0284811 A1 | 9/2016 | Yu et al. |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |

FOREIGN PATENT DOCUMENTS

| | | |
|---|---|---|
| DE | 102013012145 | 1/2015 |
| EP | 2053383 | 4/2009 |
| JP | 2018-522236 | 8/2018 |
| JP | 3403079 | 11/2018 |
| JP | 3408219 | 12/2018 |
| JP | 3408220 | 12/2018 |
| JP | 3414784 | 12/2018 |
| JP | 3420580 | 1/2019 |
| KR | 20070059880 | 6/2007 |
| WO | 200249980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007128965 | 1/2007 |
| WO | 2007054649 | 5/2007 |
| WO | 2007102960 | 9/2007 |
| WO | 2007126432 | 11/2007 |
| WO | 2009003208 | 1/2009 |
| WO | 2010022107 | 2/2010 |
| WO | 20110104245 | 9/2011 |
| WO | 2012087352 | 6/2012 |
| WO | 2012152056 | 11/2012 |
| WO | 2013096851 | 6/2013 |
| WO | 2014182630 | 7/2014 |
| WO | 2017151680 | 9/2015 |
| WO | 2015167019 | 11/2015 |
| WO | 2015176990 | 11/2015 |
| WO | 2015188197 | 12/2015 |
| WO | 2016016635 | 2/2016 |
| WO | 2016100637 | 6/2016 |
| WO | 2016196755 | 12/2016 |
| WO | 2016210986 | 12/2016 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017184677 | 10/2017 |
| WO | 2018022799 | 2/2018 |
| WO | 2018026855 | 2/2018 |
| WO | 108027335 | 5/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |

OTHER PUBLICATIONS

Stenning. The Investigation of Grain Boundary Development and Crystal Synthesis of Thin Gold Films on Silicon Wafers (2009). Retrievable at http://www.ucl.ac.uk/~ucapikr/projects/Gavin_Stenning. pdf (Year: 2009).*

(56) References Cited

OTHER PUBLICATIONS

Hanief, N., M. Topić, and C. Pineda-Vargas. "Solid-state dewetting of continuous thin platinum coatings." Nuclear Instruments and Methods in Physics Research B 363 (2015): 173-176 (Year: 2015).*

Schaefer et al. Stability and dewetting kinetics of thin gold films on Ti, TiOx, and ZnO adhesion layers. (2013). Acta Materialia 61, pp. 7841-7848 (Year: 2013).*

Thompson. "Solid-State Dewetting of Thin Films" (2012) Annual Review of Materials Research. vol. 42, pp. 399-434 (Year: 2012).*

International Search Report and Written Opinion for PCT/US17/18950 dated May 25, 2017.

Article entitled "Synthesis Mechanisms of Organized Gold Nanoparticles: Influence of Annealing Temperature and Atmosphere," published in Crystal Growth and Design publication, by Bechelany et al., vol. 10, Published 2010, pp. 587-596.

USPTO; Notice of Allowance dated Jan. 3, 2018 in U.S. Appl. No. 13/996,477.

PCT; International Search Report and Written Opinion dated Jan. 27, 2017 in Application No. PCT/US2017/015465.

PCT; International Search Report and Written Opinion dated Jan. 27, 2017 in Application No. PCT/US2017/015437.

PCT; International Search Report and Written Opinion dated Nov. 22, 2017 in Application No. PCT/US2017/044023.

PCT; International Search Report and Written Opinion dated Dec. 26, 2017 in Application No. PCT/US2017/044965.

USPTO; Requirement for Restriction dated Jan. 17, 2017 in U.S. Appl. No. 15/336,557.

USPTO; Non-Final Office Action dated May 16, 2017 in U.S. Appl. No. 15/336,557.

USPTO; Non-Final Office Action dated Oct. 19, 2016 in U.S. Appl. No. 15/220,307.

USPTO; Notice of Allowance dated Jul. 28, 2017 in U.S. Appl. No. 15/220,307.

USPTO; Requirement for Restriction dated Dec. 1, 2016 in U.S. Appl. No. 13/996,477.

USPTO; Non-Final Office Action dated May 5, 2017 in U.S. Appl. No. 13/996,477.

USPTO; Final Office Action dated Oct. 4, 2017 in U.S. Appl. No. 13/996,477.

PCT; International Search Report and Written Opinion dated Apr. 8, 2010 in Application No. PCT/US2009/054235.

PCT; International Search Report and Written Opinion dated Nov. 29, 2012 in Application No. PCT/US2011/001995.

PCT; International Search Report and Written Opinion dated Sep. 27, 2016 in Application No. PCT/US2016/039446.

PCT; International Search Report and Written Opinion dated Jul. 26. 2017 in Application No. PCT/US2017/017231.

PCT; International Search Report and Written Opinion dated Apr. 18, 2017 in Application No. PCT/US2016/68922.

H. Nishida, et al. "Self-Oriented Immobilization of DNA Polymerase Tagged by Titanium-Binding Peptide Motif," Langmuir, vol. 31, pp. 732-740, (Dec. 17, 2014).

Niwa, O. et al., "Fabrication and characteristics of vertically separated interdigitated array electrodes," Journal of Electroanalytical Chemistry and Interfacial Electrochemistry, vol. 267, pp. 291-297, (Aug. 10, 1989).

Park, S.J. et al., "Array-Based Electrical Detection of DNA with Nanoparticle Probes," Science, vol. 295, pp. 1503-1506, (Feb. 22, 2002).

Urban, M. et al., "A paralleled readout system for an electrical DNA-hybridization assay based on a microstructured electrode array," Review of Scientific Instruments, vol. 74, pp. 1077-1081, (Jan. 2003).

Choi Y.S. et al., "Hybridization by an Electroatomical Genome on Detection on Using an Indicator-Free DNA on a Microelectrode-array DNA Chip," Bulletin of the Korean Chemistry Society, vol. 26, pp. 379-383, (2005).

Park, C.W. et al., "Fabrication of Poly-Si/ AU Nano-gaps using Atomic-layer-deposited $Al_2O_3$ as a Sacrificial Layer," Nanotechnology, vol. 16, pp. 361-364, (Feb. 1, 2005).

Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005).

Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).

Schrott, W. et al., "Metal Electrodes in Plastic Microfluidic Systems," Microelectronic Engineering, vol. 86, pp. 1340-1342, (Jun. 2009).

Roy, S. et al., "Mass-Produced Nanogap Sensor Arrays for Ultra-Sensitive Detection of DNA," Journal of the American Chemical Society, vol. 131, pp. 12211-12217, (Aug. 5, 2009).

Choi, J. E. et al., "Fabrication of Microchannel with 60 Electrodes and Resistance Measurement," Flow Measurement and Instrumentation, vol. 21, pp. 178-183, (Sep. 2010).

Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).

Chen, X. et al., "Electrical Nanogap Devices for Biosensing," Materials Today, vol. 13, pp. 28-41, (Nov. 2010).

Ghindilis, A. et al., "Real Time Biosensor Platforms Fully Integrated Device for Impedimetric Assays," ECS Transactions, vol. 33, pp. 59-68, (2010).

Su, Y., "Modeling and Characteristic Study of Thin Film Based Biosensor Based on COMSO1,." Mathematical Problems in Engineering, Article 581063 (6 Pages), (Apr. 7, 2014).

Blossey, R., "Self-Cleaning Surfaces-Virtual Realities," Nature Materials, vol. 2(5), pp. 301-306, (May, 2006).

Cassie, A.B.D. et al., "Wettability of Porous Surfaces," Transitions of the Faraday Society, vol. 40, pp. 546-551, (Jan. 1944).

Choi, C. et al., "Strongly Superhydrophobic Silicon Nanowires by Supercritical CO2 Drying," Electronic Materials Letters, vol. 6 (2), pp. 59-64, (Jun. 2010).

Coulson S.R. et al., "Super-Repellant Composite Fluoropolymer Surfaces," The Journal of Physical Chemistry B., vol. 104(37), pp. 8836-8840, (Aug. 2000).

Gapin, A.I. et al., "CoPt patterned media in anodized aluminum oxide templates," Journal of Applied Physics, vol. 99(8), pp. 08G902 (1-3), (Apr. 2006).

Parkin, I. P. et al., "Self-Cleaning Coatings," Journal of Materials Chemistry, vol. 15(17), pp. 1689-1695, (Dec. 2004).

Shimoda, T. et al., "Solution-Processed Silicon Films and Transistors," Nature, vol. 440(7085), pp. 783-786, (Apr. 2006).

Kim, J. Y. et al., "Optically Transparent Glass with Vertically Aligned Surface Al203 Nanowires Having Superhydrophobic Characteristics," NANO: Brief Reports and Reviews, vol. 5(2), pp. 89-95, (Apr. 2010).

USPTO; Non-Final Office Action dated Feb. 9, 2018 in U.S. Appl. No. 15/728,400.

USPTO; Non-Final Office Action dated Feb. 23, 2018 in U.S. Appl. No. 15/728,412.

USPTO; Non-Final Office Action dated Feb. 23, 2018 in U.S. Appl. No. 15/796,080.

USPTO; Final Office Action dated Mar. 8, 2018 in U.S. Appl. No. 15/336,557.

PCT; International Search Report and Written Opinion dated Mar. 7, 2018 in Application No. PCT/US2017/063105.

PCT; International Search Report and Written Opinion dated Mar. 12, 2018 in Application No. PCT/US2017/063025.

Han, "Energy Band Gap Engineering of Graphene Nanoribbons," Physical Review Letters, vol. 98, pp. 1-7, (May 16, 2007).

Prins et al., "Room-Temperature Gating of Molecular Junctions Using Few-Layer Graphene Nanogap Electrodes," Nano Letters, vol. 11, pp. 4607-4611, (Oct. 21, 2011).

Heerema et al., "Graphene Nanodevices for DNA Sequencing," Nature Nanotechnology, vol. 11, pp. 127-136, (Feb. 3, 2016).

Liu et al., "Automatically Thin Molybdenum Disulfide Nanopores with High Sensitivity for DNA Translocation," ACS Nano, vol. 8, pp. 2504-2511, (Feb. 18, 2014).

(56) References Cited

OTHER PUBLICATIONS

Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
USPTO; Final Office Action dated Jul. 10, 2018 in U.S. Appl. No. 15/728,400.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
PCT; International Search Report and Written Opinion dated Apr. 13, 2018 in Application No. PCT/US2018/013140.
Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-523, (May 10, 2016).
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Notice of Allowance dated Oct. 11, 2018 in U.S. Appl. No. 15/796,080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.
PCT; International Preliminary Report on Patentability received Aug. 14, 2018 in Application No. PCT/US2017/017231.
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report dated Nov. 9, 2018 in Application No. PCT/US2018/048873.
PCT; Written Opinion received Nov. 9, 2018 in Application No. PCT/US2018/048873.
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Van Gerwin et al., "Nanoscaled Interdigitated Electrode Arrays for Biochemical Sensors," Sensors and Actuators B, vol. 49, pp. 73-80, (1998).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Javey et al., "Layer-By-Layer Assembly of Nanowires for Three-Dimensional, Multifunctional Electronics," Nano Letters, vol. 7, pp. 773-777, (2007).
Fan et al., "Detection of MicroRNAs Using Target-Guided Formation of Conducting Polymer Nanowires in Nanogaps," Journal of the American Chemical Society, vol. 129, pp. 5437-5443, (2007).
Kitsara et al., "Single Chip Interdigitated Electrode Capacitive Chemical Sensor Arrays," Sensors and Actuators B, vol. 127, pp. 186-192, (2007).
Xu et al., "Fabrication of Complex Metallic Nanostructures by Nanoskiving," American Chemical Society Nano, vol. 1(3), pp. 215-227, (2007).
Berdat et al., "Label-Free Detection of DNA with Interdigitated Micro-Electrodes in a Fluidic Cell," Lab on a Chip, vol. 8, pp. 302-308, (2008).
Dickey et al., "Electrically Addressable Parallel Nanowires with 30 NM Spacing from Micromolding and Nanoskiving," Nano Letters, vol. 8(12), pp. 4568-4573, (2008).
Singh et al., "3D Nanogap Interdigitated Electrode Array Biosensors," Analytical and Bioanalytical Chemistry, vol. 397, pp. 1493-1502, (2010).
Bhura, "3D Interdigitated Electrode Array (IDEA) Biosensor for Detection of Serum Biomarker," Master Thesis, Portland State University, 68 Pages, (2011).
Ino et al., "Addressable Electrode Array Device with IDA Electrodes for High-Throughput Detection," Lab on a Chip, vol. 11, pp. 385-388, (2011).
Bonilla et al., "Electrical Readout of Protein Microarrays on Regular Glass Slides," Analytical Chemistry, vol. 83, pp. 1726-1731, (2011).
Ahn et al., "Electrical Immunosensor Based on a Submicron-Gap Interdigitated Electrode and Gold Enhancement," Biosensors and Bioelectronics, vol. 26, pp. 4690-4696, (2011).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Chen et al., "Fabrication of Submicron-Gap Electrodes by Silicon Volume Expansion for DNA-Detection," Sensors and Actuators A, vol. 175, pp. 73-77, (2012).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Botsialas et al., "A Miniaturized Chemocapacitor System for the Detection of Volatile Organic Compounds," Sensors and Actuators B, Chemical, vol. 177, pp. 776-784, (2013).

(56) References Cited

OTHER PUBLICATIONS

Sanguino et al., "Interdigitated Capacitive Immunosensors with PVDF Immobilization Layers," IEEE Sensors Journal, vol. 14(4), pp. 1260-1265, (Apr. 2014).

Van Megan et al., "Submicron Electrode Gaps Fabricated by Gold Electrodeposition at Interdigitated Electrodes," Key Engineering Materials, vol. 605, pp. 107-110, (2014).

MacNaughton et al., "High-Throughput Heterogeneous Integration of Diverse Nanomaterials on a Single Single Chip for Sensing Applications," PLOS One, vol. 9(10), e111377, 7 Pages, (2014).

Kitsara et al., "Small-Volume Multiparametric Electrochemical Detection at Low Cost Polymeric Devices Featuring Nanoelectrodes," SPIE, vol. 9518, 9 Pages, (2015).

Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).

Han et al., "Redox Cycling in Nanopore-Confined Recessed Dual-Ring Electrode Arrays," Journal of Physical Chemistry C, vol. 120, pp. 20634-20641, (2016).

Okinaka et al., ""Polymer" Inclusions in Cobalt-Hardened Electroplated Gold," Journal the of Electrochemical Society, vol. 125, p. 1745, (1978).

Braun et al., "DNA-Templated Assembly and Electrode Attachment of a Conducting Silver Wire," Letters to Nature, vol. 391(6669), pp. 775-778, (Feb. 1998).

Chen et al., "Electrochemical Approach for Fabricating Nanogap Electrodes with Well Controllable Separation," Applied Physics Letters, vol. 86, pp. 123105.1-123105.3, (2005).

Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).

He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).

Hwang et al., "Electrical Transport Through 60 Base Pairs of Poly (dG)-Poly (dC) DNA Molecules," Applied Physics Letters, vol. 81(6), p. 1134-1136, (Aug. 2002).

Iqbal et al., "Direct Current Electrical Characterization of ds-DNA in Nanogap Junctions," Applied Physics Letter, vol. 86, p. 153901-1-153901-3, (Apr. 2005).

Liu et al., "Controllable Nanogap Fabrication on Microchip by Chronopotentiometry," Electrochimica Acta, vol. 50, pp. 3041-3047, (2005).

Qing et al., "Finely Tuning Metallic Nanogap Size with Electrodeposition by Utilizing High-Frequency Impedance in Feedback," Angewandte Chemie Int ed, vol. 44, pp. 7771-7775, (2005).

Reichert et al., "Driving Current Through Single Organic Molecules," Physical Review Letters, vol. 88(17), pp. 176804-1-176804-4, (Apr. 2002).

Reed et al., "Conductance of a Molecular Junction Reports," Science, vol. 278, pp. 252-254, (Oct. 1997).

Roppert et al., "A New Approach for an Interdigitated Electrodes DNA-Sensor," XVIIIth International Symposium on Bioelectrochemistry and Bioenergetics, Bioelectrochemistry, p. 143, (2005).

Kraft, "Doped Diamond: A Compact Review on a New, Versatile Electrode Material," International Journal of Electrochemistry, vol. 2, pp. 355-385, (May 2007).

USPTO; Final Office Action dated Mar. 1, 2019 in U.S. Appl. No. 15/979,135.

USPTO; Non-Final Office Action dated Mar. 6, 2019 in U.S. Appl. No. 16/015,049.

USPTO; Non-Final Office Action dated Mar. 7, 2019 in U.S. Appl. No. 15/944,356.

USPTO; Final Office Action dated Apr. 15, 2019 in U.S. Appl. No. 16/015,028.

Antibody Structure Downloaded from https://absoluteantibody.com/antibody-resources/antibody-overview/antibody-structure/ (Mar. 1, 2019).

Bai et al., "Review: Gas Sensors Based on Conducting Polymers," Sensors, vol. 7, pp. 267-307, (2007).

Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).

Khawli et al., "Charge Variants in IgG1-Isolation, Characterization, In Vitro Binding Properties and Pharmacokinetics in Rats," Landes Bioscience, vol. 2(6), pp. 613-623, (2010).

USPTO; Advisory Action dated May 22, 2019 in U.S. Appl. No. 15/979,135.

USPTO; Restriction Requirement dated May 29, 2019 in U.S. Appl. No. 16/250,929.

USPTO; Notice of Allowance dated May 30, 2019, in U.S. Appl. No. 16/152,190.

USPTO; Final Office Action dated Jun. 19, 2019 in U.S. Appl. No. 16/015,049.

USPTO; Non-Final Office Action dated Jun. 25, 2019 in U.S. Appl. No. 15/979,135.

USPTO; Non-Final Office Action dated Jul. 30, 2019 in the U.S. Appl. No. 16/015,028.

USPTO; Non-Final Office Action dated Aug. 22, 2019 in the U.S. Appl. No. 16/011,065.

USPTO; Restriction Requirement dated Sep. 19, 2019 in U.S. Appl. No. 16/073,706.

USPTO; Non-Final Office Action dated Aug. 19, 2019 in U.S. Appl. No. 12/667,583.

PCT; International Search Report and Written Opinion dated Jan. 18, 2019 in Application No. PCT/US2018/055264.

EP; European Search Report dated Jan. 30, 2019 in Application No. EP16815467.2.

CN; Notice of the First Office Action dated Sep. 2, 2019 in Chinese Application No. 201680049272.8.

EP; European Search Report dated Aug. 2, 2019 in Application No. EP16885434.7.

EP; European Search Report dated Aug. 2, 2019 in Application No. EP17745026.9.

Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).

Cosofret et al., "Microfabricated Sensor Arrays Sensitive to pH and K+ for Ionic Distribution Measurements in the Beating Heart," Analytical Chemistry, vol. 67, pp. 1647-1653, (1995).

Henry et al., "Microcavities Containing Individually Addressable Recessed Microdisk and Tubular Nanoband Electrodes," Journal of the Electrochemical Society, vol. 146(9), pp. 3367-3373, (1999).

Lin et al., "An Addressable Microelectrode Array for Electrichemical Detection," Analytical Chemistry, vol. 80, pp. 6830-6833, (2008).

USPTO; Notice of Allowance dated Oct. 23, 2019 in U.S. Appl. No. 16/250,929.

USPTO; Non-Final Office Action dated Oct. 24, 2019 in U.S. Appl. No. 16/073,706.

USPTO; Notice of Allowance dated Nov. 8, 2019 in U.S. Appl. No. 16/015,028.

USPTO; Non-Final Office Action dated Nov. 5, 2019 in U.S. Appl. No. 16/015,049.

USPTO; Notice of Allowance dated Dec. 11, 2019 in U.S. Appl. No. 15/979,135.

USPTO; Non-Final Office Action dated Jan. 10, 2020 in U.S. Appl. No. 16/076,673.

EP; European Search Report dated Oct. 24, 2019 in Application No. 17757146.

* cited by examiner

NANOPARTICLE FABRICATION

FIELD

The present disclosure relates to nanofabrication. More particularly, the present disclosure relates to the fabrication of nanoparticles.

BACKGROUND

Nanoparticles are often used in nanoengineering for diverse applications, such as being used as an attachment point for other molecules or to interact with electromagnetic radiation. A nanoparticle is generally defined as a particle between 0.1 and 100 nanometers (nm) in size.

FIGS. 1A to 1D illustrate some example uses for nanoparticles. As shown in FIG. 1A, nanoparticle 10 can serve as a carrier particle to transport deoxyribonucleic acid (DNA) molecule 12 or as an anchor point for DNA molecule 12. FIG. 1B illustrates an example where nanoparticle 10 is used for its intrinsic mechanical or chemical properties to interact with electromagnetic radiation 14. In some applications, nanoparticles 10 may be deployed in solution 18 as shown in FIG. 1C, or on solid substrate 20 as in FIG. 1D.

Nanoparticles can be composed of various materials, depending on the application. Commonly used nanoparticle materials include metals and semiconductor particles, such as quantum dots. Such particles typically have somewhat spherical or crystalline shapes.

The use of nanoparticles smaller than about 20 nm in devices, such as sensors for DNA sequencing, is often limited by current methods of fabricating nanoparticles. Even state of the art device fabrication techniques such as extreme Ultra-Violet (UV) lithography, or photolithography with phase shifting masks, and multiple patterning, will only produce nanoparticles of about 20 nm. In addition, nanoparticles smaller than 20 nm that are formed by methods such as by precipitating crystals in a solution may have a variety of different shapes. These nanoparticles may not be compatible with being placed on a surface or substrate in forming a device. The nanoparticle may then undesirably move if it is not energetically stable when placed on the surface or substrate. In addition to the need for smaller nanoparticles, there is also a need for being able to consistently fabricate nanoparticles of a defined shape that can be precisely and stably positioned on a surface or a substrate.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

DETAILED DESCRIPTION

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

Figure 1B:
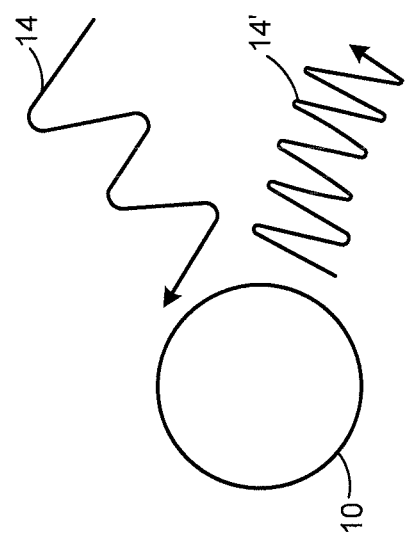
FIG. 1B shows a nanoparticle used to interact with electromagnetic radiation.
Figure 1A:
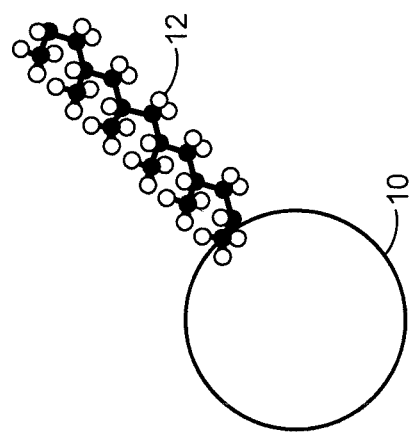
FIG. 1A shows a nanoparticle used as a carrier or contact point for a molecule.
Figure 1C:
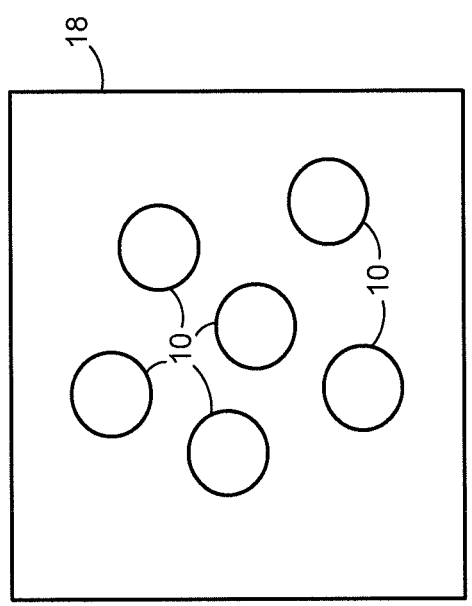
FIG. 1C shows nanoparticles used in a solution.
Figure 1D:
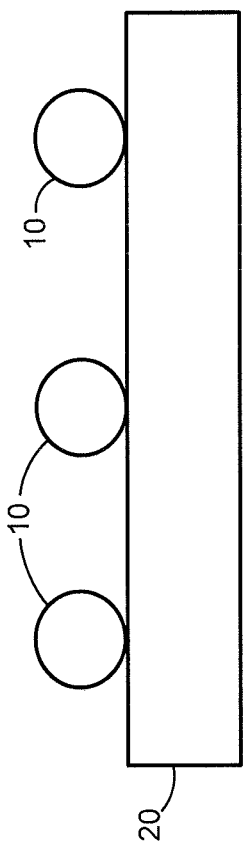
FIG. 1D shows nanoparticles to be used as contact points on a substrate.
Figure 2:
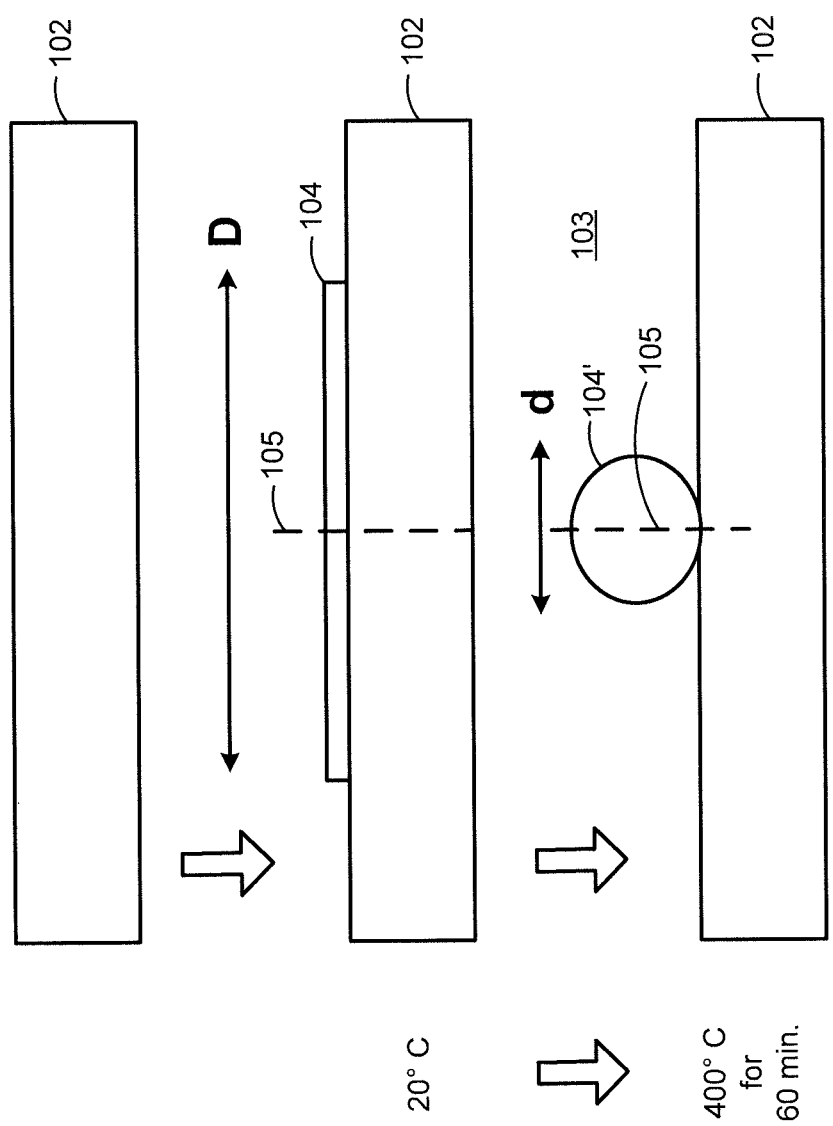
FIG. 2 provides a side view of the fabrication of a nanoparticle according to an embodiment.

FIG. 2 provides a side view of the fabrication of nanoparticle 104' according to an embodiment. Substrate 102 is provided and substance 104 is deposited or placed on substrate 102. In some implementations, a pattern generation process is used to pattern a spot or hole (not shown) in a resist (not shown) on substrate 102 centered about location 105 with a size dimension (e.g., diameter or length) or resolution of D for the pattern generation process. The spot or hole may, for example, have a round shape or a rectangular shape. In some implementations, D can range between 10 and 50 nm, but other implementations may use a different value for D. The size dimension D may correspond to the smallest size or resolution limit for a particular pattern generation process. Other implementations may not include a pattern generation process so that substance 104 is deposited onto substrate 102 without first forming a spot or hole for substance 104.

Substance 104 can be deposited as a solid-phase thin layer at a particular thickness on substrate 102 centered about location 105 using a deposition process such as sputtering or vapor deposition. Substance 104 may be deposited onto substrate 102 so that substance 104 has a round shape (e.g., disk, oval, bead), a rectangular shape (e.g., square, rectangle), or an irregular shape, as in the example embodiments of FIGS. 7 and 8 discussed below.

As shown in FIG. 2, substance 104 is heated from 20° Celsius (C) to 400° C. for a period of one hour in ambient medium 103. In the example of FIG. 2, ambient medium 103 is air at an atmospheric pressure. Other implementations may include heating substance 104 at a different pressure such as where ambient medium 103 is a vacuum. Different pressures of ambient medium 103 during heating can confer different advantages depending on the materials used for substance 104, ambient medium 103, or substrate 102.

The heating of substance 104 can be accomplished by placing substrate 102 and substance 104 in an oven. In some implementations, the heating can be part of an annealing process where substance 104 is heated to a particular temperature for a predetermined period of time and then cooled over another predetermined period of time. Heating could also be combined with or replaced by other annealing processes that allow material systems to transform to lower energy configurations. Such other annealing methods can include exposure to pressure, exposure to ultra-sound, exposure to mechanical vibration, exposure to magnetic fields, exposure to electric fields, exposure to voltage, exposure to light, UV light, or other electromagnetic radiation, or passage of electric current through a system.

Substance 104 is heated in such a way so that it beads up on substrate 102 due to cohesive forces within substance 104 being greater than adhesive forces between substrate 102 and substance 104. As a result, substance 104 is formed into nanoparticle 104' having a spherical or ball shape centered at or near the same location 105 about which substance 104 was initially located. The resulting spherical shape shown in FIG. 4 can be particularly useful to certain applications in nanoengineering and can be difficult to achieve using other processes. For example, nanoparticles that are fabricated by growing crystals in a solution may begin growing with different crystalline shapes rather than a spherical shape or other predetermined shape. This can be especially true for smaller nanoparticles. As noted above, certain nanoparticle shapes may not be conducive to being placed on a substrate or located in a fixed position due to the nanoparticle being energetically unstable when contacting a surface of the substrate.

Nanoparticle 104' also has a size dimension or resolution d that is smaller than the starting dimension or resolution D. In some implementations, the smaller size dimension d can be, for example, between 1 to 20 nm. In this regard, the smaller size dimension may or may not be smaller than a size limit of certain state of the art pattern generation processes.

The cohesive forces that cause substance 104 to contract or bead up include attractive intermolecular forces within substance 104, such as attractive Van der Waals forces. On the other hand, adhesive forces between substance 104 and substrate 102 include attractive intermolecular forces between substance 104 and substrate 102, such as electrostatic or mechanical forces. There are also relatively smaller adhesive forces between substance 104 and ambient medium 103 that can affect the ability of substance 104 to bead up, or the shape of the bead. In this regard, the adhesive forces between substance 104 and ambient medium 103 can be advantageously used to control the beading up of substance 104.

Figure 4:
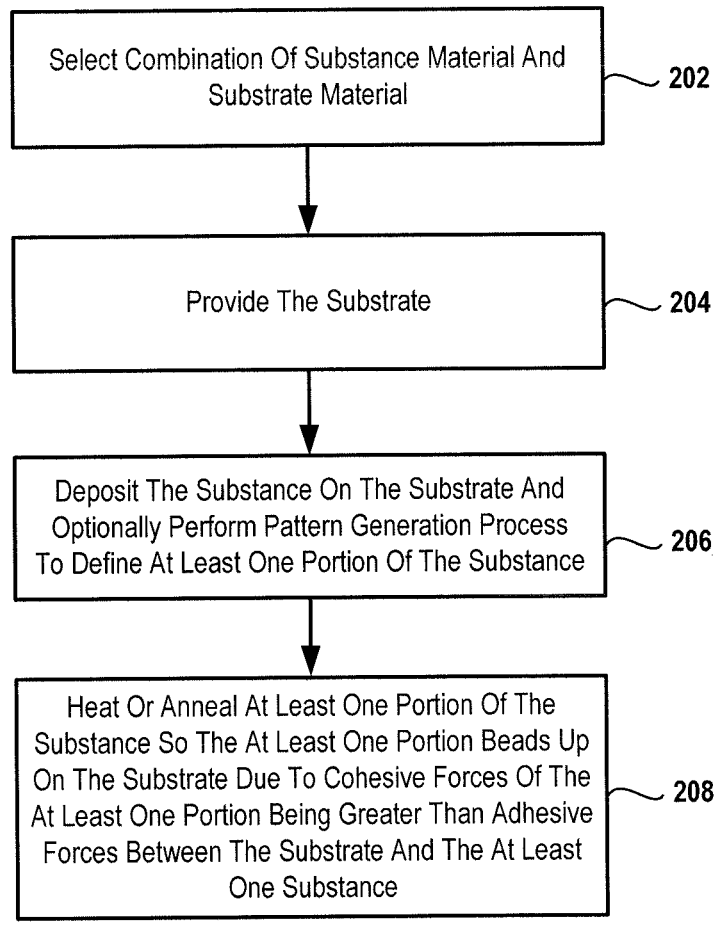
FIG. 4 is a flowchart for a nanoparticle fabrication process according to an embodiment.

As substance 104 is heated, it becomes mobile and transitions to a configuration of minimal energy or a lower energy state. Under appropriate conditions, this will cause substance 104 to contract and bead up into a shape with smaller dimension d containing the same or nearly the same volume of material. The shape of nanoparticle 104' is generally defined by the bulk and surface interaction energies of the materials used for substance 104, substrate 102, and ambient medium 103. In the example of FIG. 4, substance 104 forms a spherical shape as nanoparticle 104' due to a relatively larger surface tension of substance 104 at the interface between substrate 102 and substance 104 than at the interface between substance 104 and ambient medium 103. As discussed in more detail below with reference to FIG. 9, a lower surface tension of substance 104 at the interface with substrate 102 can result in more of a dome shape for nanoparticle 104' rather than a lenticular or spherical shape.

The temperature range at which substance 104 is heated is generally well below the melting point of substance 104. For example, in an implementation where substance 104 is gold, substrate 102 is chromium, and ambient medium 103 is air, substance 104 and substrate 102 can be heated to within a range of 390° C. to 410° C. in ambient medium 103 so that substance 104 beads up into a spherical shape over the course of approximately 50 minutes to an hour and ten minutes. In this temperature range, the gold has not reached its melting point of 1,064° C., but the cohesive forces of the gold are able to cause substance 104 to bead up.

Depending on the application, other example implementations can include a substance material such as silver, copper, aluminum, palladium, or another metal on a substrate material including chromium, platinum, palladium, titanium, silicon, or a doped silicon. Other combinations of materials for substance 104 and substrate 102 are possible. In this regard, substrate 102 may include layers of different materials.

Ambient medium 103 can include, for example, a vacuum, argon gas, nitrogen gas, air, or an oil. In other implementations, ambient medium 103 could be a solid material, such as a polymer, metal, semiconductor, or an oxide of these. The ambient medium may also be removable so that it need not be present for subsequent system processing steps or in the final finished device being fabricated. Solid mediums could be removed by the use of a solvent or selective etching process. To facilitate beading up, ambient medium 103 can be selected so that the surface tension of substance 104 at the interface with ambient medium 103 is less than at the interface with substrate 102.

Although the example of FIG. 2 indicates heating from 20° C. to 400° C. for a period of one hour, different temperatures and time periods can be used depending on the materials used for substance 104, substrate 102, ambient medium 103, and the desired shape of finished nanoparticle 104'. In particular, different temperatures and heating periods can correspond to different shapes of nanoparticle 104' based on achieving equilibrium between cohesive forces of substance 104 and adhesive forces between substance 104 and substrate 102.

As noted above, the predetermined high temperature in the beading up process is typically below the melting temperature for substance 104. In addition, the high temperature and the time for which substance 104 and other components such as substrate 102 are heated may also depend on preventing damage or alteration due to heating. For example, depending on the material used for substrate 102 or substance 104, heating above the predetermined high temperature can cause an increased risk of unwanted oxidation, corrosion, or structural damage to substance 104 or substrate 102. The application for which substance 104 and substrate 102 are to be used (e.g., antenna or current sensor) can factor into the determination of a heating temperature and heating time so that substance 104 or substrate 102 are not altered to become less useful for their intended purpose.

The size reduction from the patterning scale D to the bead scale d can be quantified assuming that the initial and final volumes of substance 104 and nanoparticle 104' are the same with:

$$V(D)=v(d) \quad \text{Equation 1}$$

Where, V is the volume of substance 104, and v is the volume of nanoparticle 104'. For the sake of illustration, the size reduction can be shown for an example where substance 104 is deposited as a disk with diameter D and thickness T, and nanoparticle 104' is a high surface tension example of a sphere of diameter d. Equating volumes provides:

$$(\pi/4)D^2T=(\pi/6)d^3 \quad \text{Equation 2}$$

or $$d=r\,D \quad \text{Equation 3}$$

where the reduction factor, r, is $$r=(3T/2D)^{1/3} \quad \text{Equation 4}$$

As an example, for a high resolution patterning process such as UV-lithography or e-beam lithography, the smallest sized disk that can be patterned may have diameter D of approximately 14 nm. The nominal thickness T, could be taken as low as a single atomic monolayer, with T of approximately 0.2 nm. Using Equation 4, the reduction factor would be r=0.28, or slightly over a 3.5-fold reduction in size below the 14 nm patterning limit, for a final diameter of approximately 3.92 nm. This reduction from a 14 nm size to a 3.92 nm size is a significant reduction in the context of current nanofabrication methods.

Figure 3:
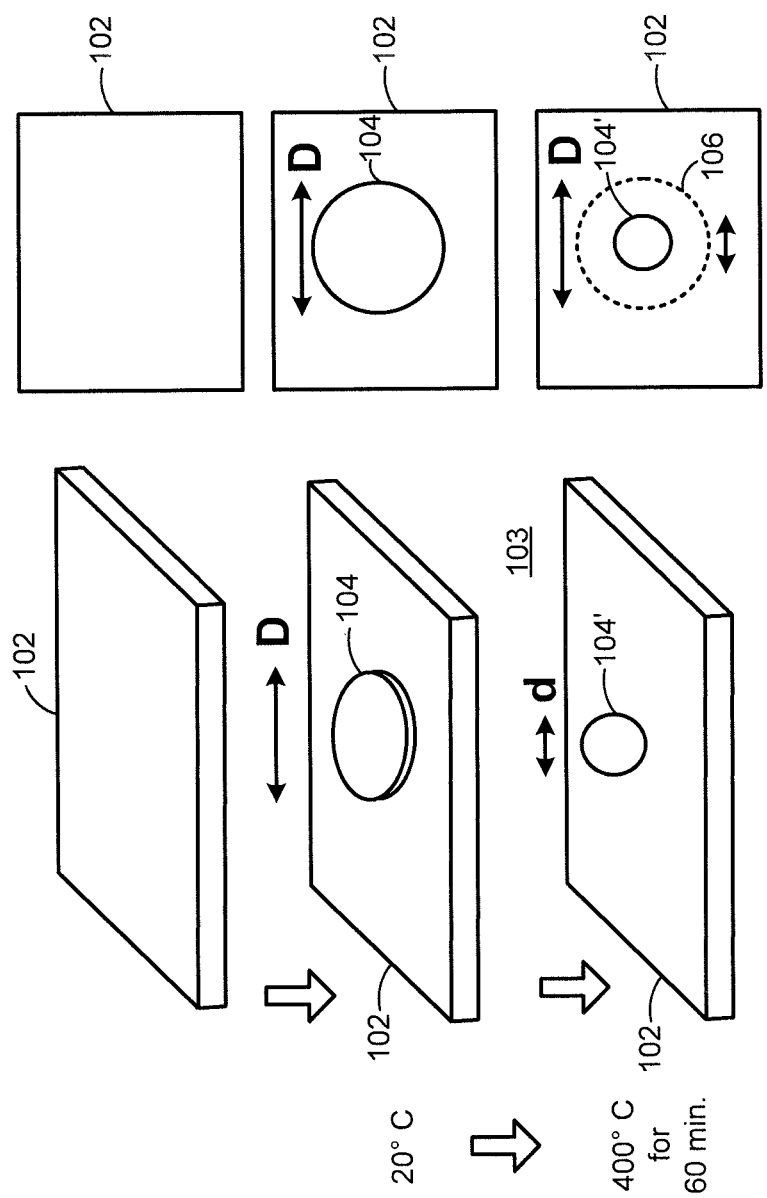
FIG. 3 provides isometric and top views of the fabrication of the nanoparticle of FIG. 2 according to an embodiment where the substance for the nanoparticle is deposited in a disk shape on a substrate.

FIG. 3 provides isometric and top views of the fabrication of nanoparticle 104' according to an embodiment. As shown in the example of FIG. 3, substance 104 is deposited on substrate 102 in the shape of a disk with a diameter of D. The heating of substance 104 at 400° C. for approximately one hour reconfigures substance 104 into a spherical or ball shape with a smaller diameter of d.

As shown in the top view of FIG. 3, finished nanoparticle 104' is located at the center of disk 104, which is indicated by the dashed circle surrounding nanoparticle 104'. The beading up process ordinarily allows for improving the finished nanoparticle 104' when compared to the initial pattern generation process or deposition process since substance 104 beads up towards its center of mass.

In addition, the sizes, shapes, and locations of multiple nanoparticles, as in an array of nanoparticles, become highly reproducible. This advantage is especially useful in nano-engineering where the scale of a finished device is at the nanometer level and relatively small variations of components can have a greater impact on the operation of the finished device.

FIG. 4 is a flowchart for a nanoparticle fabrication process according to an embodiment. In block 202, a combination of a substance material for the nanoparticle and a substrate material is selected. The selection can be based on properties of the materials such as the melting point of the materials, an ability of the substance material to attract a certain type of molecule, or the adhesive forces between the substance and substrate materials.

In some implementations, the combination of the substance material and the substrate material is selected so that the substrate beads up into a predetermined shape or beads up with a particular type of contact angle (e.g., acute or obtuse) between the substance and the substrate. For example, the substance material and the substrate material can be selected so that the adhesive forces between the substance and substrate are relatively stronger so the finished nanoparticle has more of a dome shape instead of a lenticular shape or a spherical shape.

A material for the ambient medium in which the substance will be heated can also be selected in block 202 to help facilitate a particular shape for the finished nanoparticle. In some implementations, the ambient medium is selected so that the adhesive forces between the substance and the ambient medium are negligible when compared to the adhesive forces between the substance and the substrate.

As noted above, some possible combinations of substance material and substrate material can include, for example, a metal such as gold, silver, copper, aluminum, or palladium as a substance material and at least one of chromium, platinum, palladium, titanium, silicon, or doped silicon as a substrate material. Different combinations of substrate and substance materials can result in different characteristics of the finished nanoparticle. In this regard, the selection of the substance and substrate materials can be based on design considerations for a finished device that will include the nanoparticle. For example, the finished nanoparticle may have a predetermined shape and conductivity such that the selection of the substance material for conductivity informs the selection of the substrate material to obtain the predetermined shape.

In block 204, the substrate is provided using the selected substrate material. In some implementations, a preprocessing of the substrate (e.g., a Complementary Metal-Oxide Semiconductor (CMOS) process) may take place in block 204 to form the substrate in a particular shape or provide particular layers of different materials in the substrate. In one example, a substrate layer may be patterned or etched to form the substrate into electrodes or an antenna.

In block 206, the selected substance is deposited on the substrate. In some implementations, the depositing can include a pattern generation process such as electron beam lithography, photolithography, UV lithography, extreme UV lithography, X-ray lithography, nano-imprint lithography, ion beam milling, or a CMOS lithography process that can be deployed at a CMOS fabrication facility used in manufacturing CMOS devices. The pattern generation process may also make use of other techniques such as short wavelength sources, high numerical aperture immersion, phase shifting masks, and/or multiple patterning to produce high-resolution nanoscale features.

For example, a resist material such as polymethyl methacrylate (PMMA) can be layered on the substrate in block 206 and holes or spots can be etched or patterned in the resist for holding the substance. After the substance is deposited into the holes or spots, the resist layer can be removed, such as by using a solvent in a "lift-off" process, to leave portions of the substance on the substrate that will form nanoparticles. In other implementations, the substance may be deposited directly on the substrate without using a resist or a pattern generation process. The substance can be deposited on the substrate using, for example, sputtering, chemical vapor deposition, or other deposition techniques known in the art.

In block 208, at least one portion of the deposited substance is heated or annealed so that the portion or portions bead up to form one or more nanoparticles on the substrate. The beading up can result due to cohesive forces of the portion or portions being greater than adhesive forces between the substrate and the portion or portions. In this regard, substance 104 becomes mobile and transitions to a configuration of minimal energy or a lower energy state. The amount of the substance and surface tensions between the substance and the materials contacting the substance (i.e., the substrate and the ambient medium) can determine how the substance beads up with respect to the changes in the shape of the substance and how long it takes for the substance to bead up at a particular temperature.

As discussed above, the specific temperature at which the substance is heated and the duration of heating can depend on the substance being heated and the risk of unwanted changes to the substance or other components being heated such as the substrate. Heating temperature or duration may also consider the ambient medium surrounding the substance during heating to prevent unwanted changes in the ambient medium. The examples of FIGS. 2 and 3 discussed above included heating from 20° C. to 400° C. for an hour. Other implementations may use different temperatures and heating durations based on the materials used. For most materials, the heating temperature will be between 300° C. and 600° C., and the heating duration will be within fifteen minutes and two hours. In some implementations, the high temperature can be a predetermined range such as 390° C. to 410° C. and the heating duration can be a predetermined range such as fifty minutes to 110 minutes.

In implementations where the substance is annealed, cooling of the substance can be controlled to achieve a finished quality of the nanoparticle, such as a particular hardness. In another example, the substrate and the substance are annealed so as to change electrical properties of the substrate, such as increasing the electrical conductivity, or increasing the voltage at which the system would break down or develop a short circuit.

Figure 5:
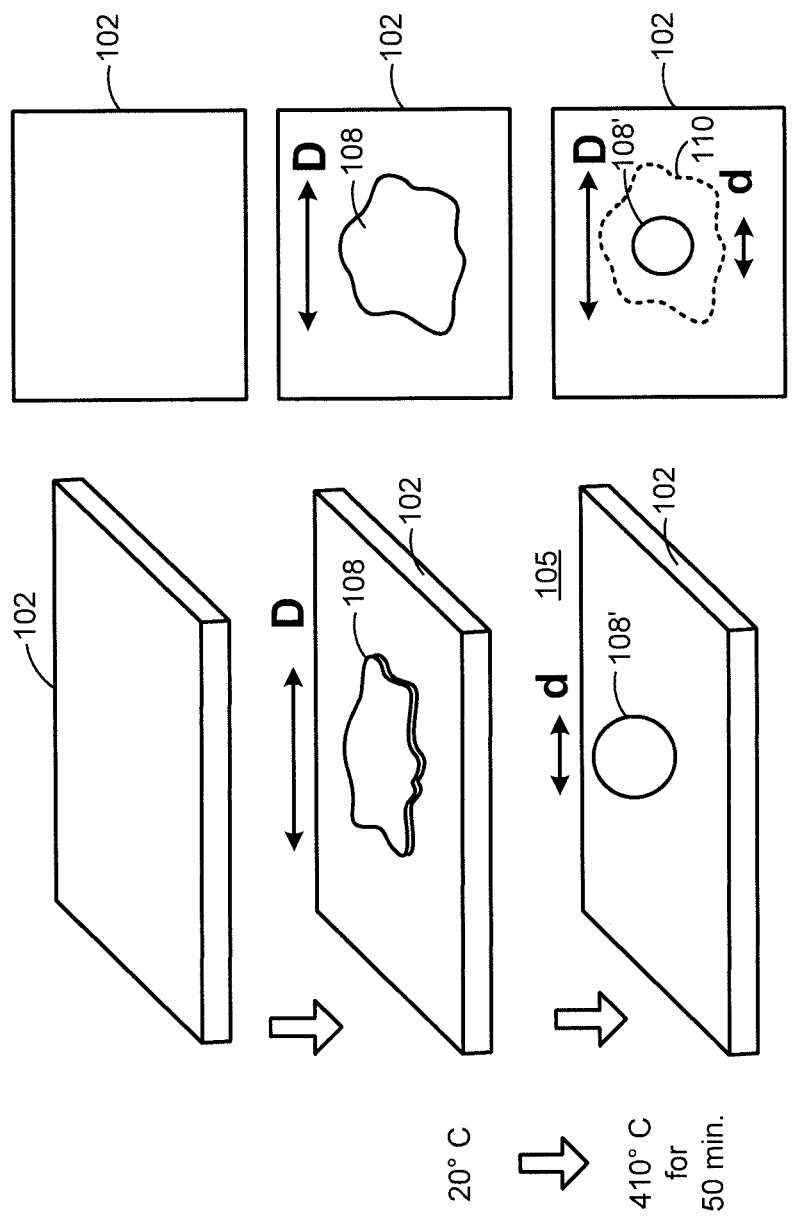
FIG. 5 provides isometric and top views of the fabrication of a nanoparticle according to an embodiment where the substance for the nanoparticle is deposited in an irregular shape on a substrate.

FIG. 5 provides isometric and top views of the fabrication of a nanoparticle where the nanoparticle material is deposited as an irregular shape on a substrate according to an embodiment. This can be the result of a deposition technique that does not include pattern generation or due to imperfections in the pattern generation process. As shown in FIG. 5, substance 108 is deposited on substrate 102 with a size dimension or length of D. Substance 108 and substrate 102 are then heated from 20° C. to 410° C. for fifty minutes. During the heating period, substance 108 beads up on substrate 102 into a spherical or nearly spherical shape as finished nanoparticle 108'. The finished nanoparticle 108' has a smaller size dimension of d than the initial size dimension of D.

As best shown in the top views of FIG. 5, nanoparticle 108' is located at a centroid or center of mass of the initial shape of substance 108, which is indicated by the dashed outline of the initial shape in the last top view of FIG. 5. The beading up of substance 108 allows for a more precise positioning of the finished nanoparticle 108'.

In addition, the finished shape of nanoparticle 108' generally does not depend on the initial shape of the deposited substance 108. In other words, the irregular shape of substance 108 when it is initially deposited of substrate 102 does not affect the final spherical shape of nanoparticle 108'. This advantage can allow for less control or a greater tolerance of the shape of substance 108 when it is initially deposited on substrate 102. In addition, a more consistent or repeatable predetermined shape of finished nanoparticle 108' is achieved by beading up substance 108 as described above.

Figure 6:
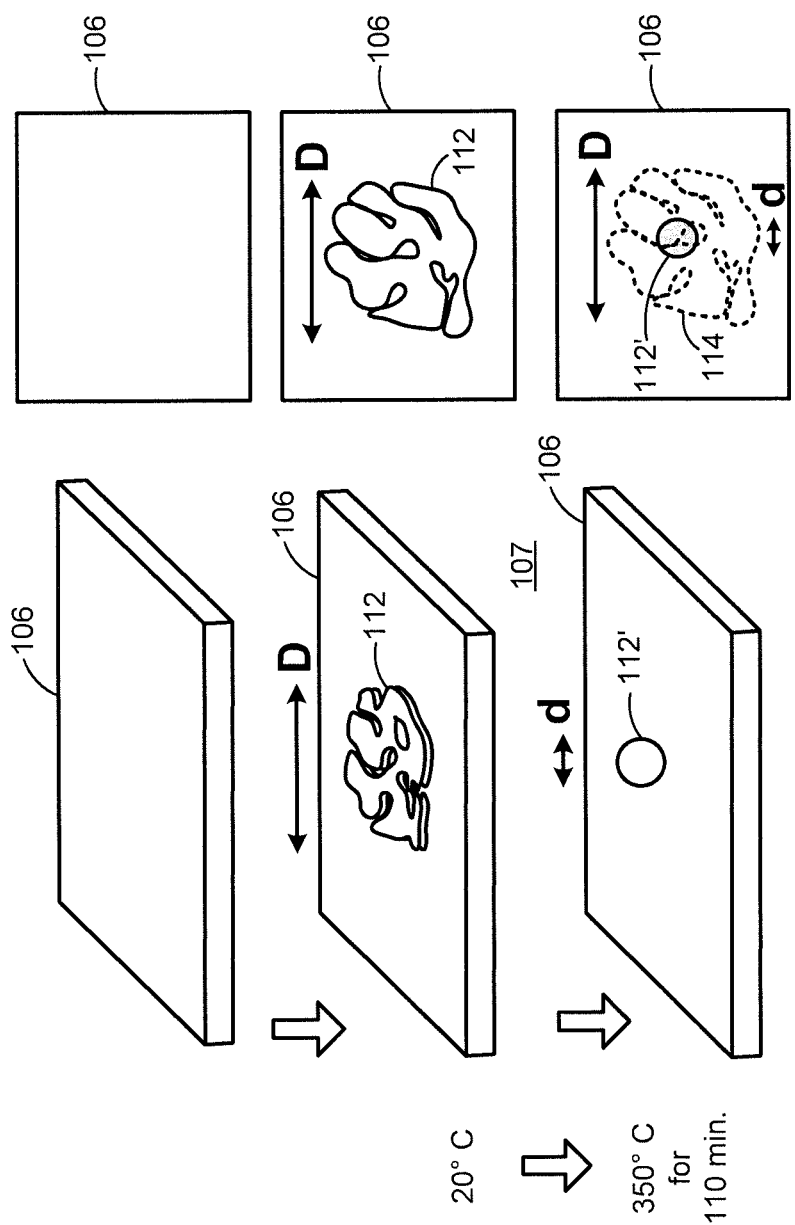
FIG. 6 provides isometric and top views of the fabrication of a nanoparticle according to an embodiment where the substance for the nanoparticle is deposited with a sub-monolayer mean thickness or with gaps in the substance.

FIG. 6 provides isometric and top views of the fabrication of nanoparticle 112' where the substance for the nanoparticle is deposited on substrate 106 with gaps in the substance or with a sub-monolayer mean thickness. A deposited sub-monolayer has an effective or mean thickness less than an atomic monolayer. In this regard, the initial layer of substance 112 can have holes or gaps so that it is not a complete layer, or a layer of a porous structure having internal gaps, bubbles, or voids. This can also include having inclusions or bubbles of another material that can become excluded or separated out during the heating process.

As shown in FIG. 6, the incomplete layer, porous layer, or sub-monolayer of substance 112 still beads up into a single, predetermined spherical shape as finished nanoparticle 112' after heating to 350° C. for 110 minutes in ambient medium 107. The starting size dimension of D, which can correspond to a resolution of a pattern generation process, can be reduced to a final size dimension or resolution of d.

The size reduction for such a porous, incomplete, or sub-monolayer of substance 112 is even more than the size reduction for a thicker layer of substance 112. This is due to the overall volume of material in such a layer being less than the volume of a full layer of substance 112 without gaps, holes, bubbles, or voids. As a result, it is ordinarily possible to achieve an even smaller finished nanoparticle 112' by depositing substance 112 with a sub-monolayer thickness or with gaps in substance 112 on substrate 106.

For example, using Equations 1 to 4 discussed above with reference to FIG. 2, if only 10% of a complete atomic monolayer of 0.2 nm thickness is deposited to provide an effective or mean thickness of T=0.02 nm in the 10 nm diameter disk pattern, the resulting size reduction factor for a sphere with diameter d would be r=0.14 with d=1.4 nm. This provides slightly over a seven-fold reduction in size, as compared to the three-fold reduction in size for the previous example discussed above where substance 104 in FIG. 2 was deposited as a single atomic monolayer of approximately 0.20 nm. The deposition of a sub-monolayer can therefore produce an even smaller nanoparticle that still has a predetermined shape. Note, that a similar result is obtained if the 10 nm disk is deposited at a depth of 2 nm but with the initial material having a porosity of 99% (i.e., 99% void). The effective thickness T of the material would again be 0.02 nm, or 1% of the initial thickness of 2 nm.

Figure 7:
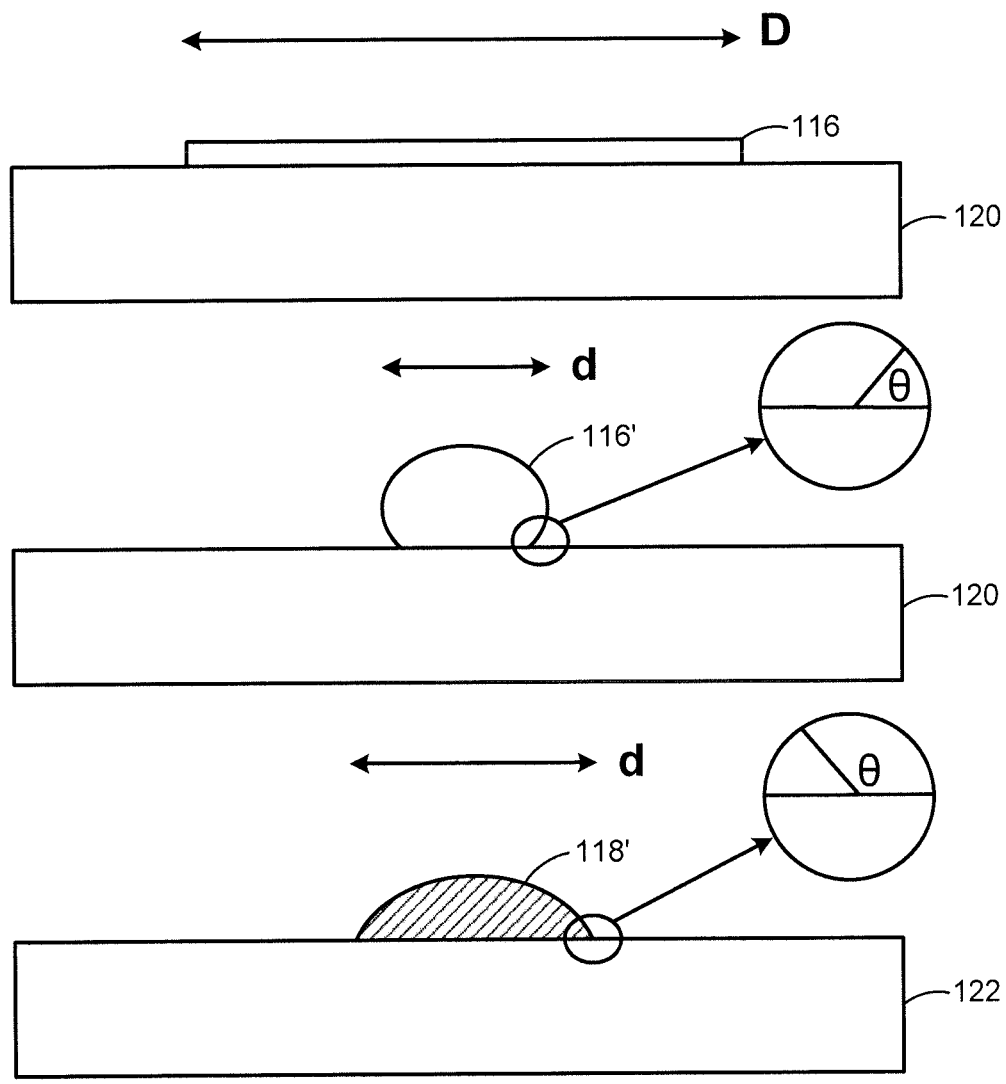
FIG. 7 provides side views of the fabrication of nanoparticles made of different substances on different substrate materials so that the combination of the substrate material and the substance material results in different predetermined nanoparticle shapes according to an embodiment.

FIG. 7 provides side views of the fabrication of nanoparticles made of different substances on different substrate materials so that the combination of the substrate material and the nanoparticle material results in different predetermined nanoparticle shapes according to an embodiment. As shown in FIG. 7, substance 116 is deposited on substrate 120 with a size dimension or resolution of D. After heating, substance 116 forms nanoparticle 116' having a predetermined lenticular shape where the contact angle between nanoparticle 116' and substrate 120 is acute. The contact angle can be within a predetermined range of angles such as, for example, between 0° and 90°, 90° and 170°, 45° and 90°, or 90° and 135°.

On the other hand, a different substance heated on a different substrate 122, forms nanoparticle 118' having a different predetermined dome shape where the contact angle θ between nanoparticle 118' and substrate 122 is obtuse. The difference in shape for the finished nanoparticles 116' and 118' is due to different configurations of the substance when it reaches an equilibrium point between cohesive forces within the substance and adhesive forces surrounding the substance (i.e., at the substrate and at the ambient medium). The final shape can also be viewed as the configuration of the substance that provides equilibrium between the substance's surface tensions at the substrate interface and at the ambient medium interface.

In other examples, the difference in the final shape of the nanoparticle can be based on the temperature to which the substance is heated. The combination of the substance material and the substrate material, and/or the temperature to which the substance is heated can be selected to obtain a desired contact angle within a predetermined range of angles between the substance and the substrate.

Figure 8B:
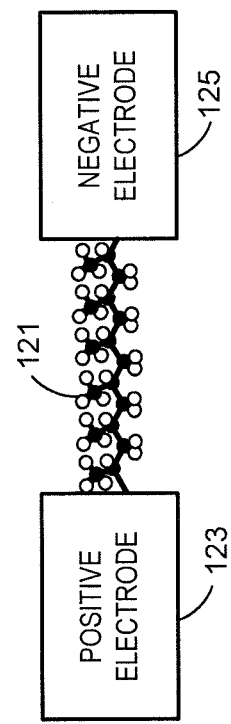
FIG. 8B shows the molecular circuit of FIG. 8A after assembly.
Figure 8A:
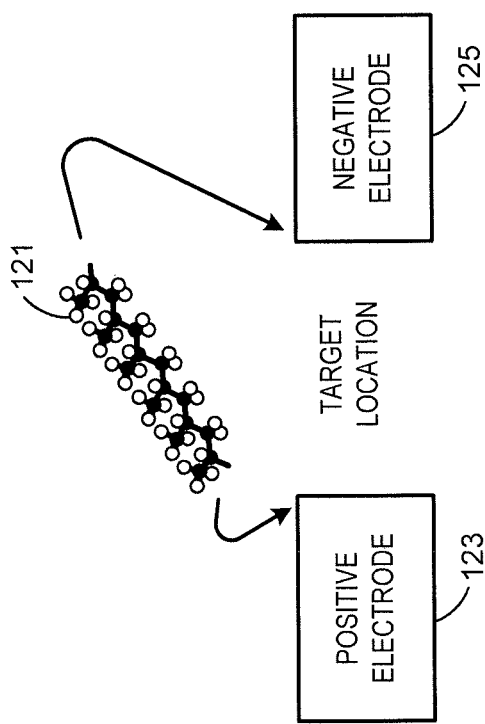
FIG. 8A shows the assembly of a molecular circuit.

FIGS. 8A and 8B illustrate the assembly of a molecular circuit where molecule 121 is positioned between electrodes 123 and 125 to obtain information about molecule 121. In implementations where molecule 121 is DNA, the molecular circuit can allow for the sequencing of molecule 121 based on its electrical properties.

Figure 9B:
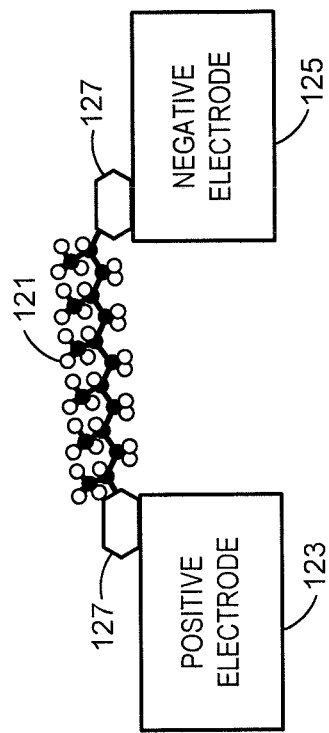
FIG. 9B shows the molecular circuit of FIG. 9A after assembly.
Figure 9A:
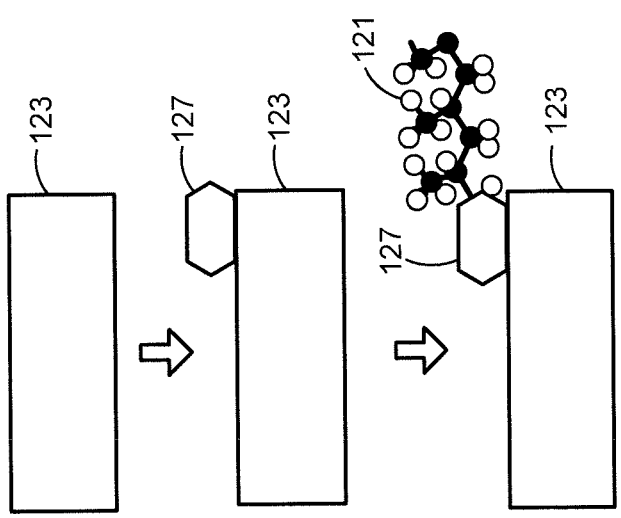
FIG. 9A shows the assembly of a molecular circuit using a contact point.

The use of nanoparticles 127 on electrodes 123 and 125 in FIGS. 9A and 9B can improve the mechanical and electrical connections between molecule 121 and electrodes 123 and 125. Nanoparticles 127 can be made of a material that selectively binds to molecule 121 to provide a guided self-assembly into the molecular circuit shown in FIG. 9B. However, it is often difficult to precisely position nanoparticles 127 on electrodes 123 and 125 and to maintain their location using conventional methods. Aspects of the nanoparticle fabrication processes discussed above can be used to precisely position nanoparticles 127 on electrodes 123 and 125, as discussed below in more detail.

Figure 10:
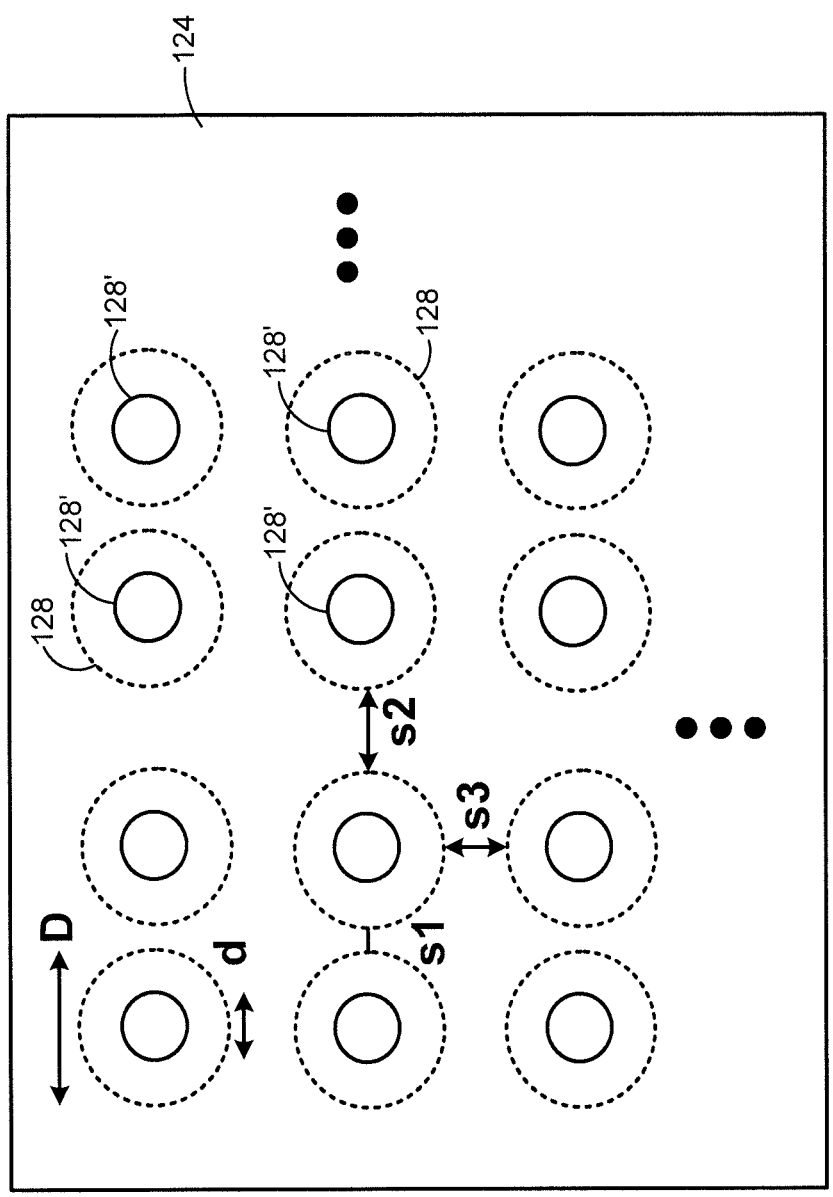
FIG. 10 provides a top view of an array of nanoparticles formed on a substrate according to an embodiment.

FIG. 10 provides a top view of an array of nanoparticles 128' formed on substrate 124 according to an embodiment. A pattern generation process can be performed to provide a specified array pattern with a predetermined spacing or spacings between deposited portions of substance 128, as indicated by s1, s2, and s3 in FIG. 10. These initial spacings can lead to predetermined final spacings between finished nanoparticles 128' after heating or annealing.

The array of FIG. 10 can be produced by heating or annealing all of the portions of substance 128 to efficiently form nanoparticles 128' at the same time. The final array includes nanoparticles 128' all having approximately the same predetermined shape and a reduced size dimension or resolution of d. In addition to the advantageous size reduction below certain patterning limits, heating or annealing the portions of substance 128 provides a reproducibility of a predetermined shape and location for nanoparticles 128'. The final nanoparticles 128' are located at or near the centers of the initial deposited portions of substance 128 so as to obtain a relatively consistent spacing between nanoparticles 128' in the array.

Figure 11:
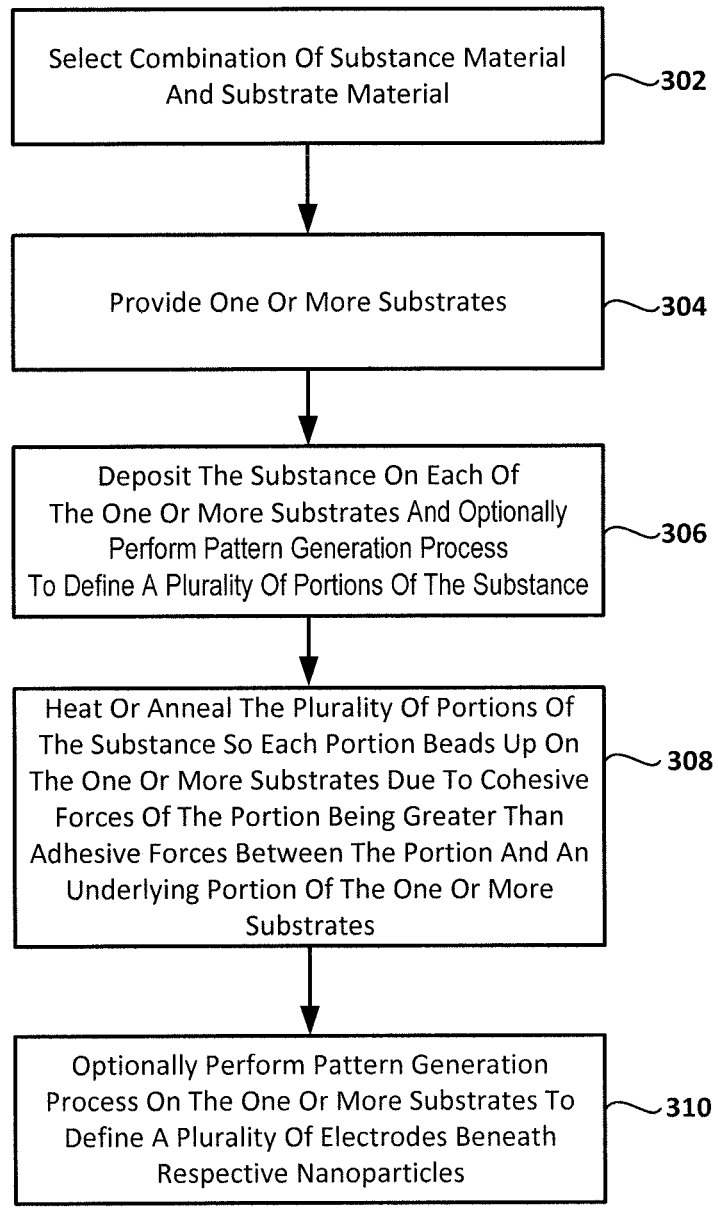
FIG. 11 is a flowchart for fabricating a plurality of nanoparticles according to an embodiment.

FIG. 11 is a flowchart for fabricating a plurality of nanoparticles according to an embodiment. In block 302, a combination of a substance material for the nanoparticle and a substrate material are selected. The selection can be based on properties of the materials such as the melting point of the materials, an ability of the substance material to attract a particular molecule, or the adhesive forces between the substance and substrate materials.

In some implementations, the combination of the substance material and the substrate material is selected so that portions of the substrate bead up into nanoparticles each having a predetermined shape or with a particular type of contact angle (e.g., acute or obtuse) between the portion and the substrate. For example, the substance material and the substrate material can be selected so that the adhesive forces are relatively stronger so the finished nanoparticle shape has more of a dome shape instead of a lenticular shape or a spherical shape.

A material for the ambient medium in which the substance will be heated can also be selected in block 302 to help facilitate a particular shape for the finished nanoparticles. In some implementations, the ambient medium is selected so that the adhesive forces between the substance and the ambient medium are negligible when compared to the adhesive forces between the substance and the substrate. One example can include an implementation where the ambient medium is a vacuum, as produced by the use of vacuum pumping systems available on materials processing equipment As noted above, some possible combinations of substance material and substrate material can include, for example, a metal such as gold, silver, copper, aluminum, or palladium as a substance material and at least one of a chromium, platinum, palladium, titanium, silicon, and doped silicon substrate material. Different combinations of substrate and substance materials can result in different characteristics of the finished nanoparticle. The selection of the substance and substrate materials can be based on design considerations for a finished device that will include the nanoparticles.

In block 304, one or more substrates are provided using the selected substrate material. In some implementations, an initial processing of the substrate or substrates (e.g., via a CMOS process) may take place in block 304 to form the substrate or substrates in a particular shape or with particular layers of different materials. In one example, an initial substrate layer may be patterned or etched to form multiple substrates as electrodes or antennas.

In block 306, the substance is deposited on one or more substrates. The substance can be deposited on the substrate or substrates using, for example, sputtering, chemical vapor deposition, or other deposition techniques known in the art.

In some implementations, the depositing can include a pattern generation process such as electron beam lithography, photo lithography, UV lithography, extreme UV lithography, X-ray lithography, nano-imprint lithography, ion beam milling, or a CMOS fabrication facility etching process to define multiple portions of the substance. The pattern generation process may also make use of other techniques such as short wavelength sources, high numerical aperture immersion, phase shifting masks, and/or multiple patterning to produce high-resolution nanoscale features.

In block 308, the portions of the substance are heated or annealed so that the portions bead up to form nanoparticles on the substrate. The beading up can result from cohesive forces of the portions being greater than adhesive forces between the substrate and the portions. In this regard, the portions become mobile and transition to a configuration of minimal energy or a lower energy state. The amount of the substance and surface tensions between the substance and the materials contacting the substance (i.e., the substrate and the ambient medium) determines how the substance beads up with respect to the changes in the shape of the portions and how long it takes for the portions to bead up at a particular temperature.

As discussed above, the specific temperature at which the substance is heated and the duration of heating can depend upon the substance being heated and the risk of unwanted changes to the substance or other components that are being heated. Heating temperature or duration may also consider the ambient medium surrounding the substance during heating to prevent unwanted changes in the ambient medium.

In implementations where the substance is annealed, cooling of the substance can be controlled to achieve a finished quality of the nanoparticle, such as a particular hardness. In another example, the one or more substrates and the substance are annealed so as to change electrical properties of the one or more substrates.

In block 310, an optional pattern generation process may be performed on the one or more substrates to define electrodes beneath respective nanoparticles. In one example, the nanoparticles may first be formed on a single substrate and then a pattern generation process may be performed to remove portions of the substrate to define multiple electrodes in the substrate.

Figure 12:
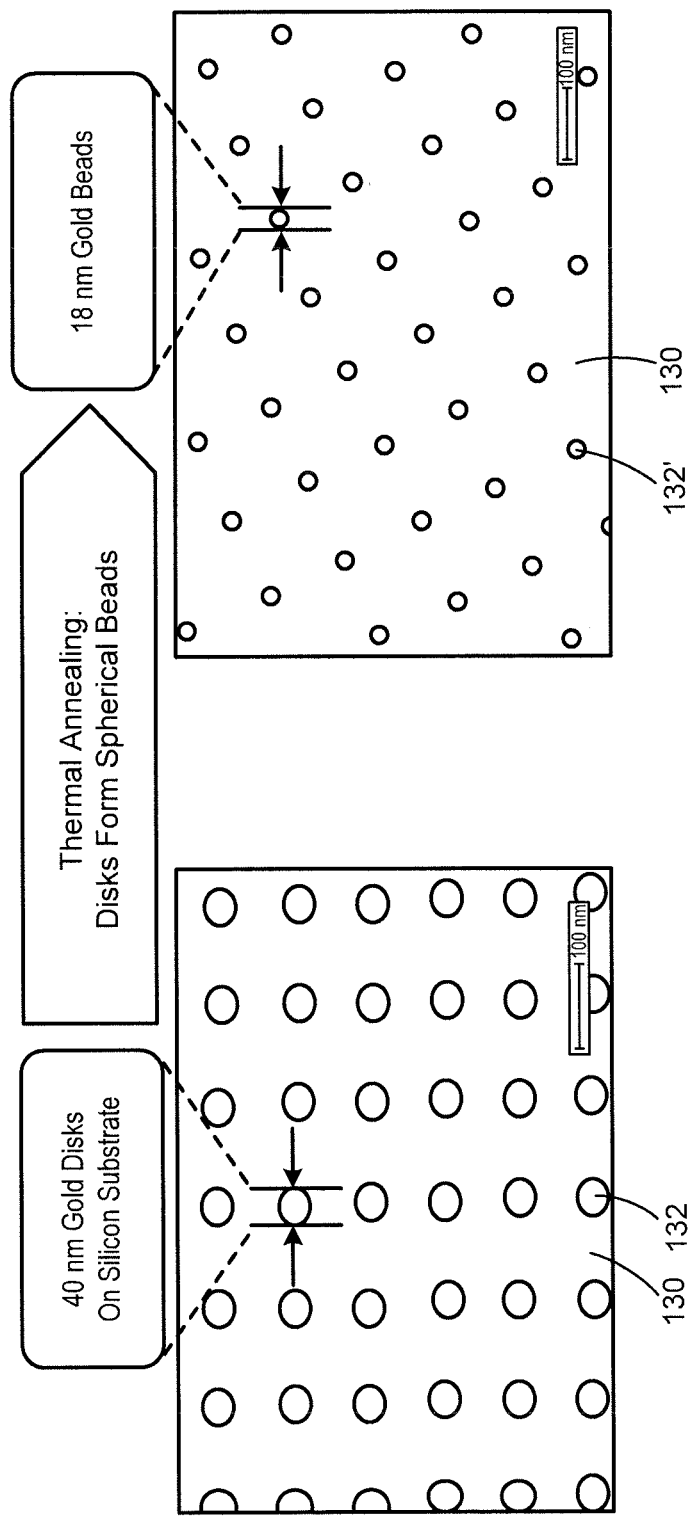
FIG. 12 represents before and after images of an array of disks that have been annealed into an array of beads having a smaller size dimension than the disks according to an embodiment.

FIG. 12 represents before and after electron microscope images of an array of disks 132 that have been annealed into an array of beads 132' having a smaller size dimension than the disks 132 according to an embodiment. As shown in the example of FIG. 12, 40 nm diameter gold disks 132 are deposited on silicon substrate 130. Gold disks 132 are patterned on the silicon substrate 130 using e-beam lithography of a polymer resist such as PMMA to make an initial pattern of holes in the resist in which the gold is deposited using sputtering. The resist is removed via a lift off process to result in the pattern of 40 nm diameter gold disks 132 shown on the left side of FIG. 12.

After annealing substrate 130 and gold disks 132, the disks 132 form nanoparticles in the form of 18 nm diameter gold beads 132' that are centered at the same points as the central portions of the original gold disks 132'. The process of FIG. 12 results in a 55% size reduction of the deposited gold disks and simultaneously transforms the shape of all of the disks 132' into a predetermined bead shape.

Figure 13:
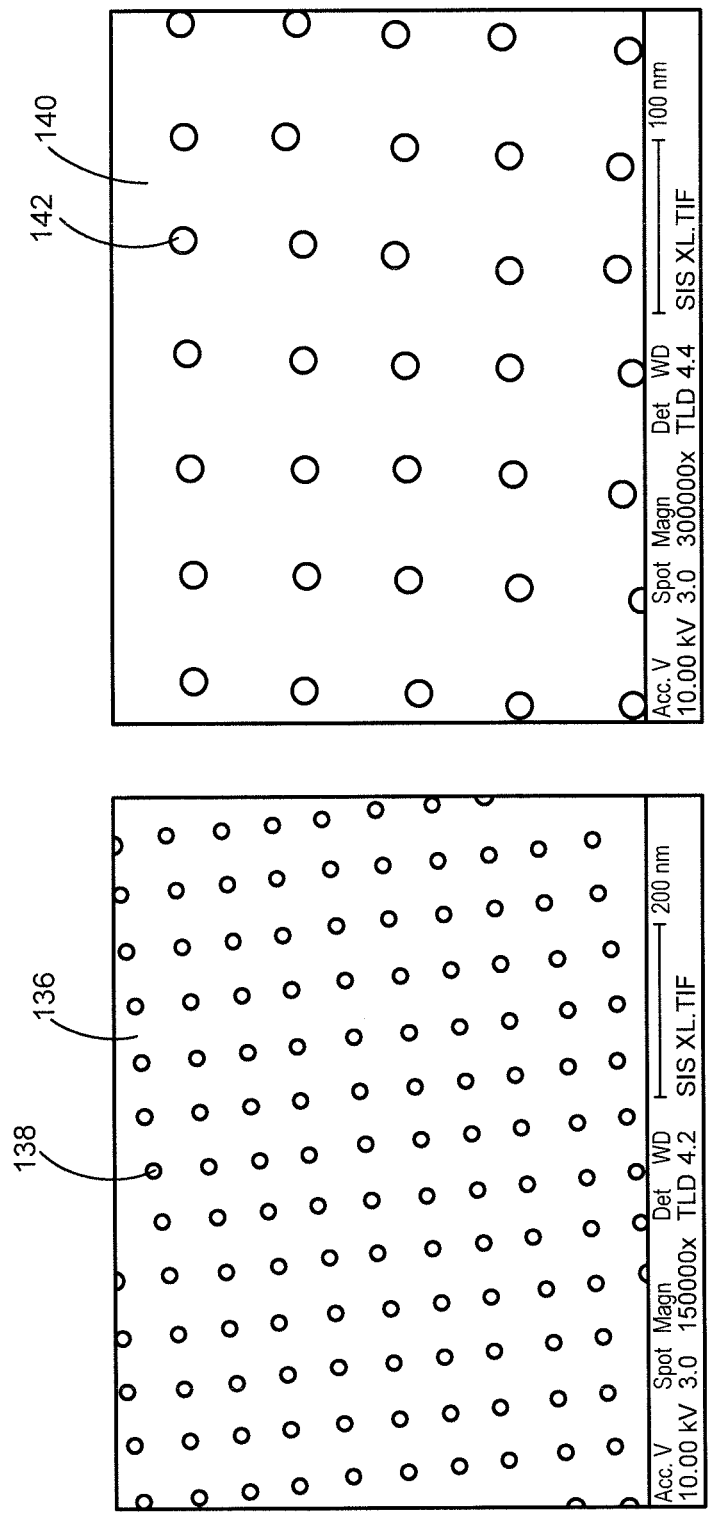
FIG. 13 represents images of an initial spot pattern of holes in a resist and an array of beads formed from depositing a substance in the holes and annealing the deposited substance according to an embodiment

FIG. 13 represents electron microscope images of an initial spot pattern of holes 138 in PMMA resist 136 and an array of nanoparticles 142 formed on silicon substrate 140 from depositing a thin layer of gold in holes 138 and annealing the deposited gold according to an embodiment. Holes 138 are patterned using e-beam lithography at a pattern resolution limit of 11 nm, meaning that holes 138 have a diameter of approximately 11 nm. A thin layer of gold is deposited using sputtering into the holes 138 and lift-off or removal of resist 136 leaves gold disks deposited on substrate 140.

The gold disks are annealed in a vacuum as an ambient medium at a high temperature of 400° C. to yield the array of gold nanoparticles 142. Each of the nanoparticles 142 have a bead shape and a diameter between 4 and 8 nm, thereby achieving diameter reductions of up to approximately 60% relative to the diameter of the initial material deposited. In this regard, the scale of the left image is 200 nm and the scale of the right image is 100 nm. The resulting nanoparticles 142 are super-resolved below the pattern generation limit of 11 nm for e-beam lithography and have a consistent shape and spacing.

Figure 14:
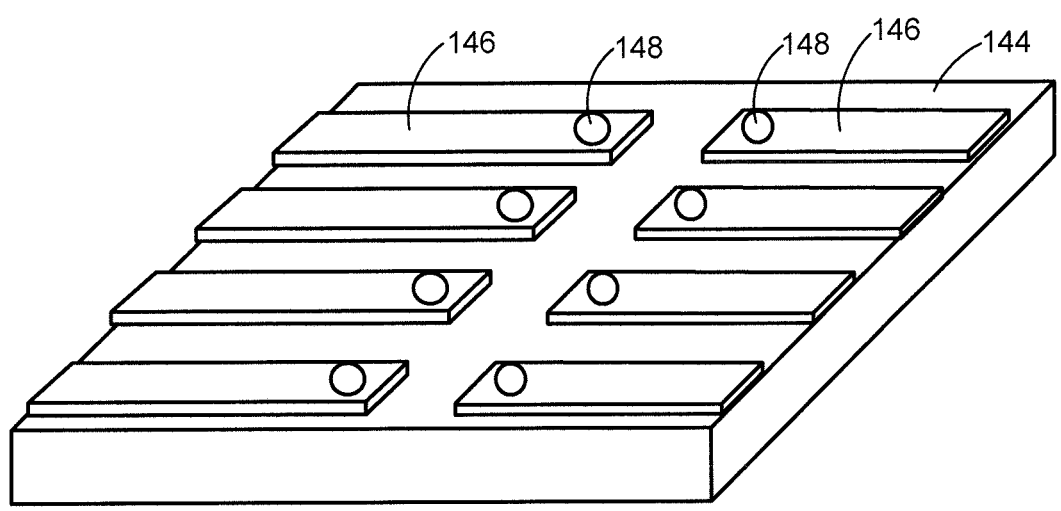
FIG. 14 is an isometric view of an array of nanoparticles formed on a plurality of electrodes according to an embodiment

FIG. 14 is an isometric view of an array of nanoparticles 148 formed on a plurality of electrodes 146 on chip 144 according to an embodiment. In some implementations, chip 144 can form part of an integrated circuit. The arrangement shown in FIG. 14 can be used, for example, to form an array of molecular circuits where a certain type of molecule attaches between the pairs of electrodes 146 with nanoparticles 148 serving as contact points for attaching the molecules between the electrodes.

In some implementations, the array can be used for different DNA applications depending on the scale of the array. In one example, an array with more than 100 nanoparticles can be used to form electrodes for a molecular electronics sensor array with the capacity for DNA fingerprinting on a DNA sample. In another example, an array with more than 10,000 nanoparticles can be used to form electrodes for a molecular electronics sensor array with the capacity to sequence a DNA fragment including approximately 100 bases. In yet another example, an array with more than 1,000,000 nanoparticles can be used to form electrodes for a molecular electronics sensor array with the capacity to sequence an entire human genome. The nanoparticle fabrication processes described above ordinarily allow for the simultaneous formation of a large number of nanoparticles (e.g., 100 to 1,000,000,000) to efficiently produce large scale arrays. In addition, the foregoing nanoparticle fabrication processes provide a predetermined and consistent shape that can be smaller than a resolution limit of current state of the art patterning processes.

In the example of FIG. 14, electrodes 146 are located on chip 144 and may be formed before or after depositing the substance material on the substrate. Nanoparticles 148 are located on end portions of electrodes 146 by depositing a substance material centered on each end portion location. Heating or annealing the substance material causes the substance material to form into a spherical shape located at or near a center location of the end portion.

Figure 15:
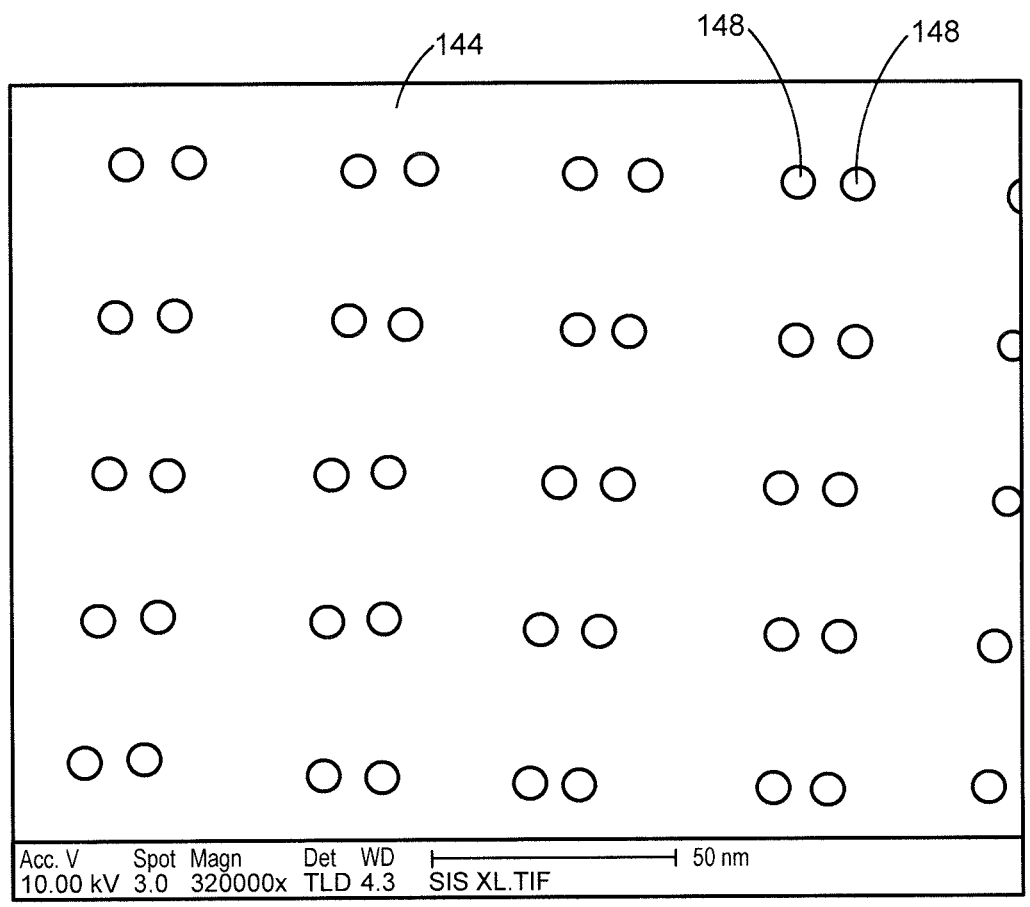
FIG. 15 represents an image of the array of nanoparticles of FIG. 14 according to an embodiment.

FIG. 15 represents an electron microscope image of the array of FIG. 14 according to an embodiment. As shown in FIG. 15, nanoparticles 148 are arranged as contact points on chip 144. Each nanoparticle 148 is positioned on an end portion of an electrode (not shown) with a 4 to 8 nm diameter following e-beam lithography for pattern generation in a resist, sputtering of gold into holes of the resist, and annealing at 400° C. in a vacuum. The pairs of nanoparticles 148 are spaced between 10 to 15 nm apart from each other. As demonstrated by FIG. 15, the foregoing processes can achieve nanoparticles that are smaller than a resolution limit of current pattern generation processes and provide nanoparticles with a reproducible and predetermined shape and spacing.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the present disclosure. The described embodiments are to be considered in all respects only as illustrative and not restrictive, and the scope of the disclosure is therefore indicated by the following claims rather than by the foregoing description. All changes which come within the meaning and range of equivalency of the claims are to be embraced within their scope.

What is claimed is:

1. A method for fabricating a nanoparticle on a substrate, the method comprising:
   depositing a substance directly onto the substrate by a pattern generation process that defines an at least one portion of the deposited substance having a diameter D and an effective thickness T; and
   heating the at least one portion of the substance at a temperature less than the melting temperature of the substance and for a time sufficient so that the at least one portion of the substance beads up on the substrate due to cohesive forces of the at least one portion of the substance being greater than adhesive forces between the substrate and the at least one portion of the substance, thereby forming the nanoparticle on the substrate, wherein the substance consists of a first metal, wherein the first metal consists of gold, silver, copper, or aluminum, and the substrate consists of a second metal, wherein the second metal consists of platinum or palladium, and wherein the effective thickness T is selected to provide a nanoparticle diameter d with a reduction factor r of less than about 1.0, and wherein $d=r\,D$ and $r=((3T)/(2D))^{1/3}$.

2. The method of claim 1, wherein depositing the substance includes performing a pattern generation process to define each portion of the at least one portion of the substance to have a size dimension, and wherein heating the at least one portion of the substance reduces the size dimension of each portion of the at least one portion of the substance in forming the at least one nanoparticle.

3. The method of claim 1, wherein the at least one portion of the substance is heated to bead up into at least one nanoparticle having a spherical shape.

4. The method of claim 1, further comprising selecting a combination of one substance material and one substrate material so that the at least one portion of the substance beads up into a predetermined shape on the substrate during heating.

5. The method of claim 1, further comprising selecting a combination of one substance material and one substrate material or a temperature at which to heat the at least one portion of the substance to obtain a contact angle within a predetermined range of angles between the at least one portion of the substance and the substrate during or following heating of the at least one portion of the substance.

6. The method of claim 1, wherein heating the at least one portion of the substance includes heating the at least one portion of the substance to a temperature between 300 and 500 degrees Celsius.

7. The method of claim 1, wherein heating the at least one portion of the substance includes heating the at least one portion of the substance and the substrate in an ambient medium, the ambient medium including a vacuum, argon gas, nitrogen gas, air, an oil, a polymer, a metal, or a semiconductor material.

* * * * *